US 6,581,539 B1

(12) United States Patent
Rasor

(10) Patent No.: US 6,581,539 B1
(45) Date of Patent: Jun. 24, 2003

(54) PACKAGE AND HOLDER FOR DISPENSER

(76) Inventor: Ned S. Rasor, 15601 Montebello Rd., Cupertino, CA (US) 95014-5404

( * ) Notice: Subject to any disclaimer, the term of this patent is extended or adjusted under 35 U.S.C. 154(b) by 233 days.

(21) Appl. No.: 09/638,501

(22) Filed: Aug. 15, 2000

Related U.S. Application Data

(60) Provisional application No. 60/148,736, filed on Aug. 16, 1999.

(51) Int. Cl.$^7$ .......................... B65D 85/00; B65D 25/56
(52) U.S. Cl. ...................... 116/284; 116/215; 116/305; 116/DIG. 32; 206/459.1; 73/149; 73/290 R
(58) Field of Search .................................. 116/284, 290, 116/296, 298, 299, 305, 309, 215, 200, DIG. 32; 206/459.1, 459.5; 73/149, 290 R; 220/631, 603, 669

(56) References Cited

U.S. PATENT DOCUMENTS

| 2,707,930 | A | * | 5/1955 | Miles | 116/200 |
| 5,785,048 | A | | 7/1998 | Koerner | 128/200.23 |
| 5,860,552 | A | * | 1/1999 | Culhane et al. | 220/212 |
| 5,864,097 | A | | 1/1999 | Alvino | 177/232 |
| 6,257,410 | B1 | * | 7/2001 | Ulmann et al. | 206/389 |

* cited by examiner

Primary Examiner—Diego Gutierrez
Assistant Examiner—R. Alexander Smith
(74) Attorney, Agent, or Firm—Jill L. Robinson

(57) ABSTRACT

A holder and/or a holder and cover for containing a dispenser of a consumable product, such as a cartridge containing pressurized gas for therapeutic use, and a method for selecting the optimum parameters for such holder are provided to allow sensitive determination of the amount product remaining in the dispenser. The holder has a curvilinear or partly curvilinear circumference, and holds the dispenser so that the center of mass of the dispenser and the product it contains is at a predetermined optimum location relative to the center of mass of the holder. Thus, when the holder is placed on a horizontal surface, the holder can roll along the curvilinear circumference, and the predetermined optimum relationship of the center of mass of the dispenser and the center of mass of the holder causes the holder to come to rest at adequately spaced unique locations on the circumference of the holder depending upon the combined mass of the dispenser and the product it contains. Markings placed on the external surface of the holder can then be used to determine the amount of product remaining in the container. The holder is preferably made of plastic and can be composed of a fluorescent plastic to permit the dispenser to be easily located, grasped and removed for use, and then replaced after use, even in the dark.

23 Claims, 5 Drawing Sheets

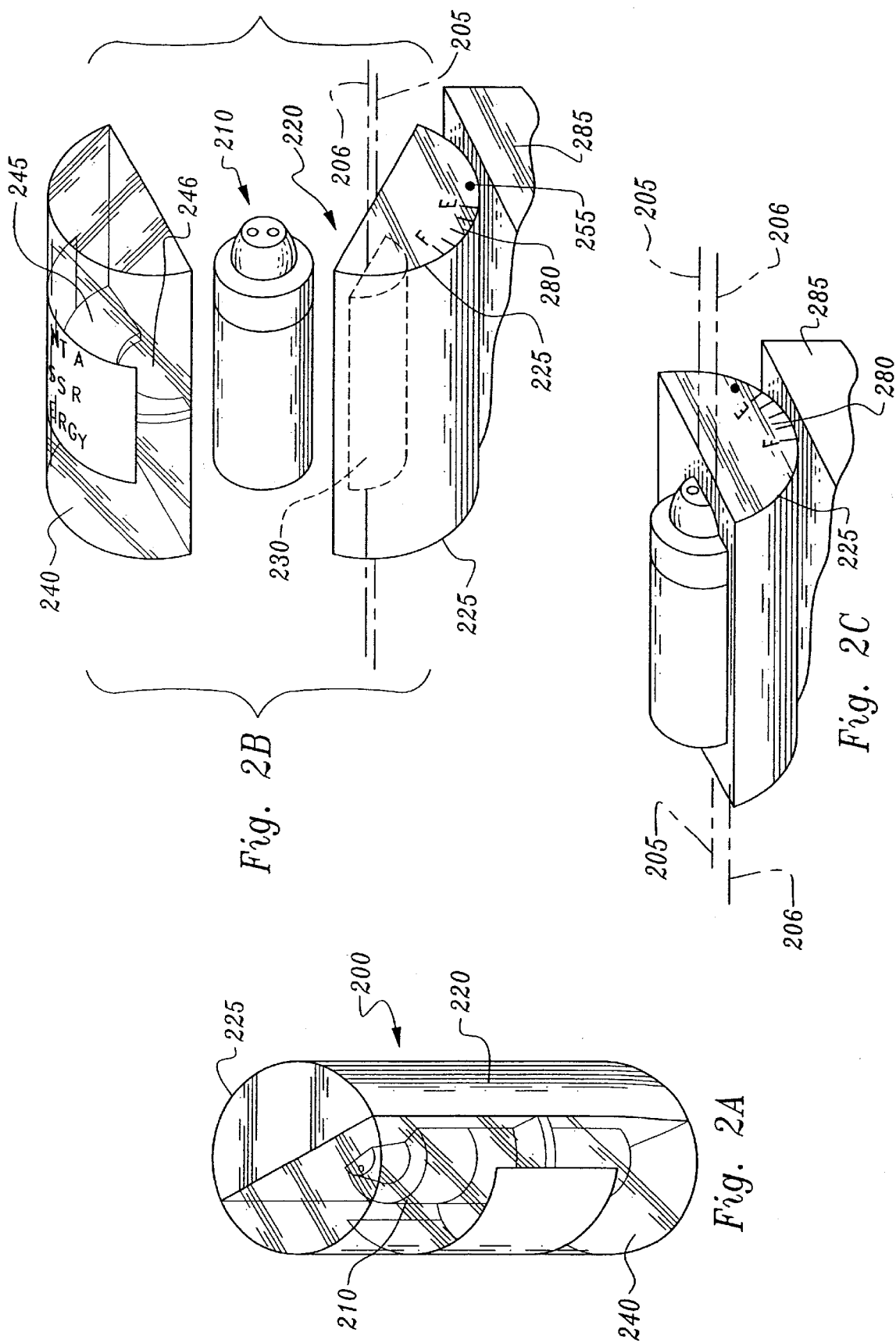

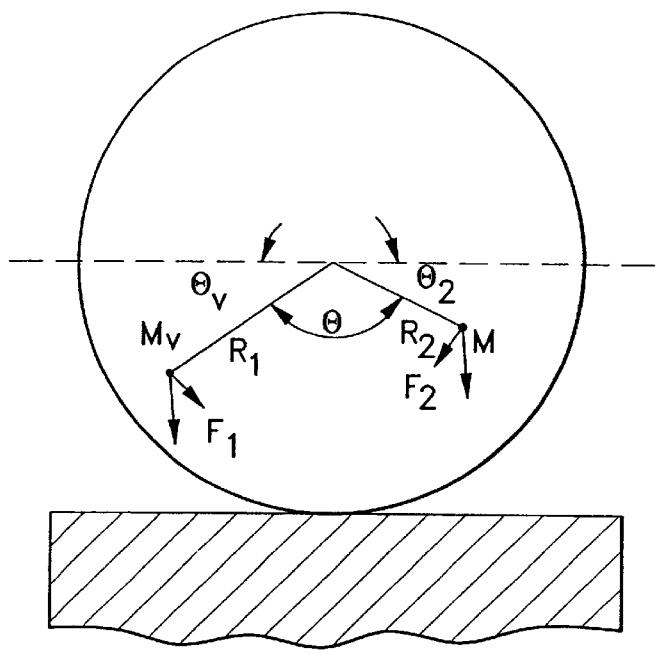
*Fig. 4A*
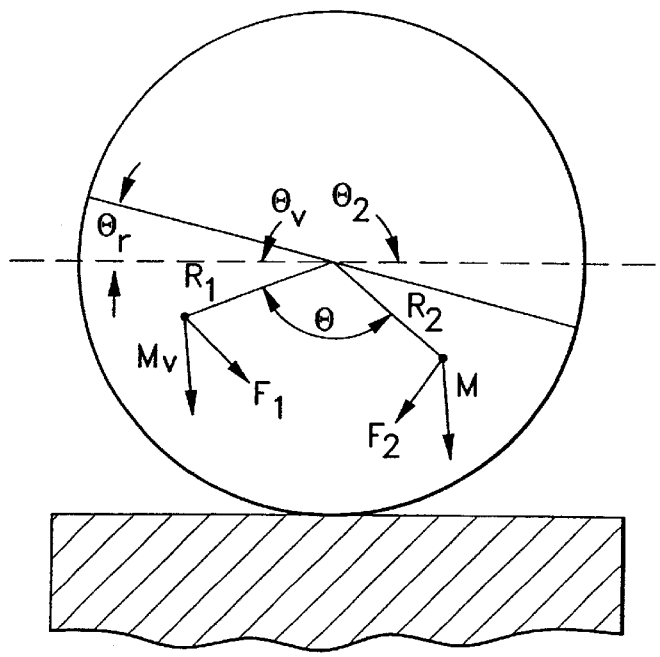
$\Theta_r = 0$ for $\alpha = 1$
*Fig. 4B*
$\Theta_v + \Theta + \Theta_2 + 180°$
*Fig. 4C*
$F_1 = M_v \cos \Theta_v$
*Fig. 4D*
$F_2 = M \cos \Theta_2$
*Fig. 4E*
$F_1 R_1 = F_2 R_2$
*Fig. 4F*
$\Theta_v = 180° - \Theta - \mathrm{acos}(\alpha \cos \Theta_v)$
where $\alpha = R_1 M_v / R_2 M$
*Fig. 4G*
$\Theta_r = (180° - \Theta)/2 - \Theta_v$
*Fig. 4H*

PACKAGE AND HOLDER FOR DISPENSER

CROSS-REFERENCE TO RELATED APPLICATION

This application claims the benefit of U.S. Provisional Patent Application No. 60/148,736, filed Aug. 16, 1999, which is incorporated by reference herein.

BACKGROUND OF THE INVENTION

This invention concerns a package for shipping and a stand for holding the gas dispenser described in the following U.S. Provisional Applications for Patent:

Application No. 60/164,125 filed on Nov. 8, 1999 by Julia S. Rasor and Ned S. Rasor, entitled "Dispenser Innovations;"

Application No. 60/185,495 filed on Feb. 28, 2000 by Ned S. Rasor and Julia S. Rasor, entitled "Alternate Physiologic Means;"

and in the following U.S. Patent Application:

Application No. 09/614,389, filed on Jul. 12, 2000 by Ned S. Rasor and Julia S. Rasor, entitled "Method and Apparatus for Relieving Headaches, Rhinitis and other Common Ailments," which claims the benefit of U.S. Provisional Patent Application No. 60/143,164, filed Jul. 12, 1999, each of which is incorporated by reference herein.

Certain products require specialized containers and/or dispensers to hold the product and dispense appropriate amounts of the product in the desired form when required. Examples of such products and their associated containers and dispensers are described in U.S. Patent Application No. 09/614,389, and in U.S. Provisional Application Nos. 60/164,125 and 60/185,495. Each of these applications describes the potential use of pressurized cartridges that contain $CO_2$, or other therapeutic gas or agents, and associated dispensing apparatus for providing controlled amounts of gas to the nose, mouth, ear and eye for use in the control of headaches, respiratory and eye allergy attacks, among other ailments. However, certain specialized containers and dispensers (hereinafter individually and collectively referred to as "dispensers") such as the pressured cartridges described, by necessity do not allow the user to visually determine the amount of the product remaining in the dispenser. Furthermore, it is desirable that such dispensers be protected during shipping, storage and marketing. It is also desirable to provide a suitable means of identifying the product within the dispenser for marketing purposes and to provide a container that allows easy use of the dispenser. It is therefore an object of the invention to provide a holder for the specialized dispenser that allows the user to easily determine the amount of dispensed agent remaining in the dispenser. It is a further object of the invention to provide an optional cover that protects and identifies the dispenser during shipping, storage and marketing, and that together with the holder, completely encloses and fixedly holds the dispenser. It is a further object of the invention to provide a holder that becomes an adjunct for convenient use of the dispenser after the cover has been removed.

SUMMARY OF THE INVENTION

The current invention comprises a holder and/or a holder and cover adapted to hold a dispenser such as a pressurized gas cartridge. The holder has at least a partially curvilinear circumference, such as is found in a substantially cylindrical or semi-cylindrical form having a circular or semi-circular base. The holder is adapted to securely, but removably, hold the dispenser such that the center of mass of the dispenser and the product it contains is at a predetermined location relative to the center of mass of the holder. Thus, when the holder is laid on its side on a horizontal surface so that the holder can roll along the circumference, the predetermined relationship of the center of mass of the dispenser and the center of mass of the holder cause the holder to come to rest at unique locations along the circumference depending upon the combined mass of the dispenser and the product it contains. Markings placed on the external surface of the holder can then be used to indicate the amount of product remaining in the dispenser. The bolder is preferably made of plastic and can be composed of a fluorescent plastic to permit the dispenser to be easily located, grasped and removed for use, and then replaced after use, even in the dark.

Depending upon the form of the holder, a cylindrical or semi-cylindrical cover, preferably of clear plastic may be attached fixedly to but removably from the base, thereby further protecting the dispenser. The cover can include a label on its inner or outer surface with printed information identifying the product for marketing purposes and briefly describing its use or alternatively a booklet can be inserted inside the package cover such that the identification and other brief description on its cover page are readable through the package cover. In addition, a product logo or other decorative design can be molded or otherwise inscribed in the cover.

Other features and advantages of the current invention will appear from the following description in which the preferred embodiments have been set forth in detail in conjunction with the accompanying drawings.

BRIEF DESCRIPTION OF THE DRAWINGS

FIG. 2a shows a second embodiment of the invention as might be found in an assembled package on a store shelf FIG. 2b shows the second embodiment of the invention with the cover and the dispenser removed from the holder.

FIG. 2c shows the second embodiment of the invention with the holder in use to indicate the amount of product remaining in the dispenser.

FIG. 4a schematically shows the base of the holder and the relative positions of the centers of mass of the dispenser/product and the holder for a full dispenser.

FIG. 4b schematically shows the base of the holder and the relative position of the centers of mass of the dispenser/product and the holder is less than fill where the angle of displacement from the horizontal is shown as an angle $\theta_r$.

FIG. 4c is an equation describing the angular relationship of the centers of mass.

FIG. 4d is an equation describing the gravitational forces on masses $M_y$ resolved into tangential forces $F_1$.

FIG. 4e is an equation describing the gravitational forces on masses M resolved into tangential forces $F_2$.

FIG. 4f is an equation describing the condition under which free rotation of the holder ceases.

FIG. 4g is an equation describing the relationship of variable angle $\theta_y$ to the parameter $M_yR_1/MR_2$ and the fixed angle $\theta$, as shown graphically in FIG. 5a.

FIG. 4h is an equation describing the angular change from the initial position of the holder with the full dispenser in place.

DETAILED DESCRIPTION OF THE DRAWINGS

Figure 1A:
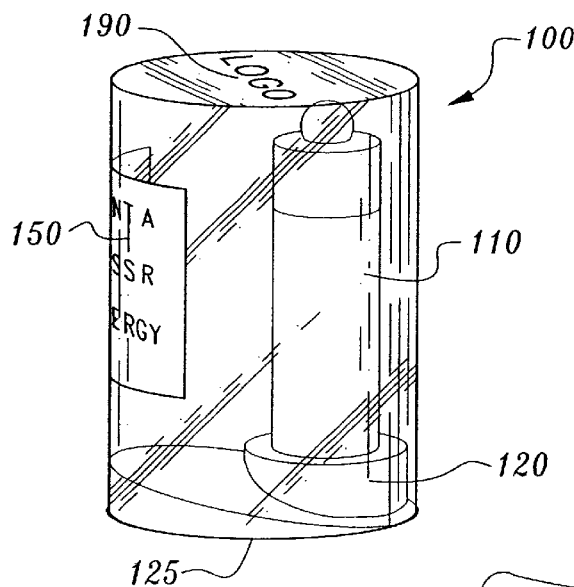
FIG. 1a shows a first embodiment of the invention as might be found in an assembled package on a store shelf.
Figure 1B:
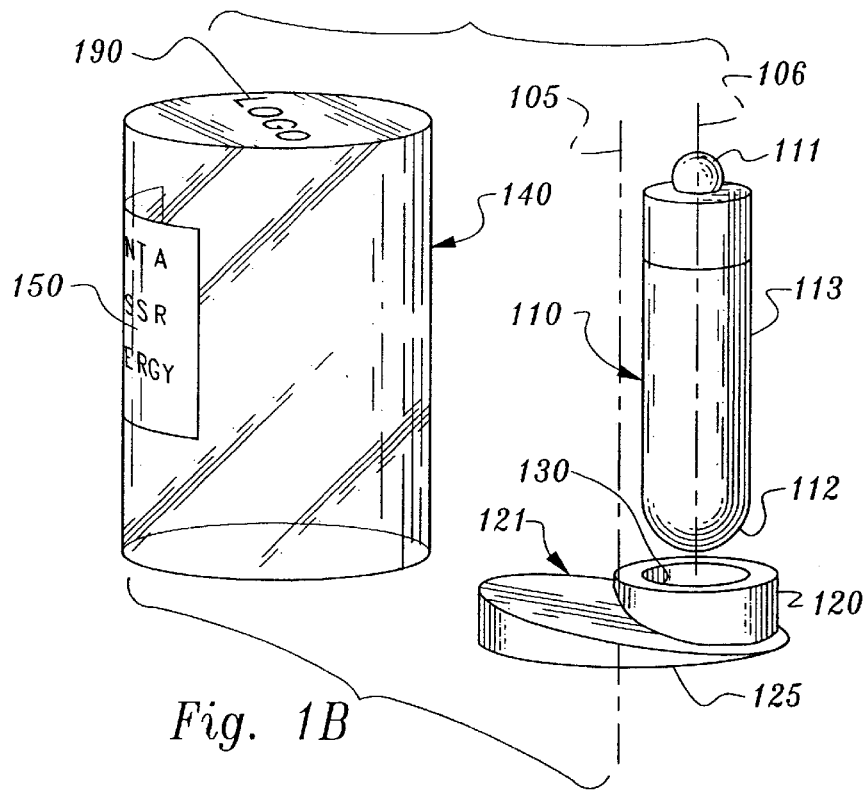
FIG. 1b shows the first embodiment of the invention with the cover and the dispenser removed from the holder.
Figure 1C:
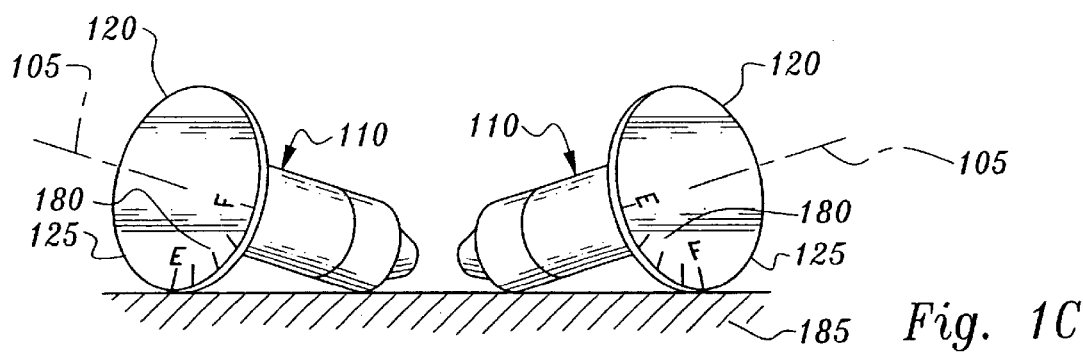
FIG. 1c shows the first embodiment of the invention with the holder in use without the cover, indicating the amount of product remaining in the dispenser.

With reference to FIGS. 1a–c, a generally cylindrical package 100 is shown in which the dispenser 110 stands upright in a cylindrical holder 120 comprising a substantially circular base 121 that defines a curvilinear circumference 125 and further defines a well 130.

The dispenser 110 may include a cartridge 113 and associated dispenser head apparatus 111 for containing under pressure and dispensing $CO_2$ or a mixture including $CO_2$ and/or other physiologically active substances. One such cartridge contains approximately 16 grams of $CO_2$ and weighs approximately 60 grams when completely full. The dispenser head apparatus 111 is usually mounted on the top of the cartridge 113, which includes the sealing cap or similar structure. The bottom of the cartridge 112 is often rounded. The well 130 is designed so that the bottom of the cartridge 113 may be easily inserted and easily removed, yet so that the dispenser 110 may also be securely held in either an upright or substantially horizontal position.

The holder also defines a central axis 105 and is designed to roll about the central axis 105 along the curvilinear circumference 125. The well 130 defines a second axis 106, which is displaced from the central axis 105 in order to allow for correct positioning of the center of mass of the holder 120 relative to the center of mass of the dispenser 110 and the product it contains, when the dispenser 110 is seated in the well 130 as further described in connection with FIGS. 4a–b.

An enclosing cover 140 is a substantially cylindrical, preferably transparent, cap that fits over the dispenser 110. The cover 140 may be attached fixedly to but removably from the holder 120. This may be accomplished by a number of means well-known in the art, including forming the cover 140 and/or the base 121 of a slightly resilient plastic and causing the interior circumference of the cover 140 to be slightly larger than the exterior circumference of the base 121. When fixedly attached to the base 121, the cover 140 protects the dispenser 110, and if an appropriate height, can confine the dispenser 10 so that it remains fully seated in the well 130.

The cover 140 can include a label 150 on its inner or outer surface with printed information identifying the product for marketing purposes and briefly describing its use. Instead of a fixed label on the surface of the cover 140, a booklet (not shown) can be inserted inside the package cover 140 such that the identification of the product and other brief descriptions on its cover page are readable through the package cover 140, with detailed instructions on use of the dispenser 110 being on its interior pages. After the booklet is removed, the cover 140 and holder 120 with their matching and stylish exterior design are free of marketing and other labels, thereby becoming an attractive article on a desk or night stand, for example. In addition to a label and/or booklet, a product name, logo or other decorative design 190 can be molded or otherwise inscribed in the cover 140.

The holder 120 design permits the dispenser 110 to be easily located, grasped and removed for use, and then replaced after use. The holder 120 may be constructed of a fluorescent plastic that glows in the dark to facilitate its location and use in a darkened room.

A second preferred embodiment of the invention is shown in FIG. 2. The generally cylindrical package 200 for the dispenser 210 again comprises a cover 240 and holder 220. In this embodiment, The holder 220 is a cradle-like, half-circular cylinder that defines a partially curvilinear circumference 225, a central axis of rotation 205, and a well 230 into which the dispenser 210 may be inserted. In contrast to the embodiment shown in FIG. 1, the well 230 is elongated and is adapted to receive and retain the side of dispenser 210. The well 230 also defines a central axis 206 offset from the central axis of the holder 205 to allow for correct positioning of the center of mass of the holder 220 relative to the center of mass of the dispenser 210 and the product it contains, when the dispenser 210 is seated in the well 230 as further described in connection with FIGS. 4a–b.

As in the first embodiment, the holder 220 is preferably composed of fluorescent plastic which glows in the dark.

The cover 240 is a mating half-cylindrical shell that may be fixedly but removably attached to the holder 220 by any of a number of means well-known in the art, and includes an interior retainer component 245 that keeps the dispenser fully seated in the well 230 when the cover 240 is attached to the holder 220. As in the first embodiment, the cover 240 is preferably of transparent plastic. The interior retainer component 245 may be comprised of a half-circle of material with a radius approximately equal to the interior radius of the cover 240 permanently attached to or unitarily molded from the interior wall of the cover 240. The interior retainer component 245 forms a cut-out portion 246 positioned on the retainer 245 and shaped to closely fit along the external circumference of the dispenser 210 when the cover 240 is attached to the holder 220. The precise position and shape of the cut-out 246 are dependent upon the shape of the dispenser and the position of the well 230 within the holder 220, which is selected to meet the criteria described in connection with FIGS. 4a–b.

The assembled package 200 usually would stand upright when on display, with its cylindrical axis 205 vertical. In use, however, the cover 240 would be removed and the holder 220 would be placed to lie with the curvilinear circumference 225 resting on a horizontal surface, with the central axis 205 horizontal.

Labeling and decoration of the package is similar to that described for the first preferred embodiment, including the possible use of a booklet inside the cover 240 with labeling on its cover page.

Figure 3A:
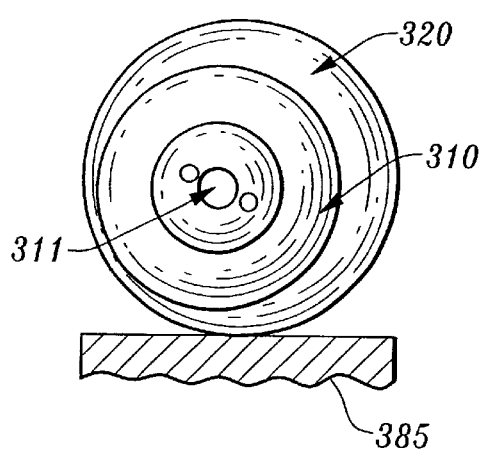
FIG. 3a schematically shows the top view of a third embodiment of the invention lying on a flat, horizontal surface.
Figure 3B:
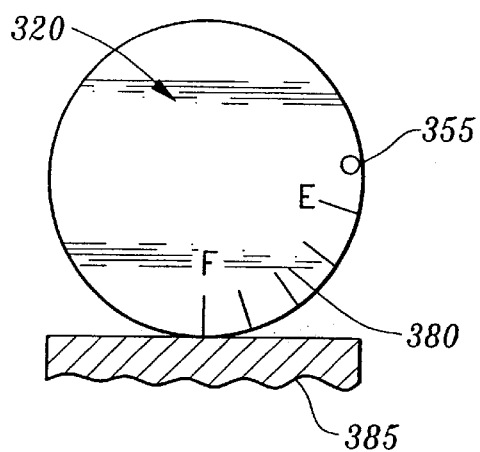
FIG. 3b schematically shows the bottom view of the third embodiment of the invention lying on a flat, horizontal surface.
Figure 3C:
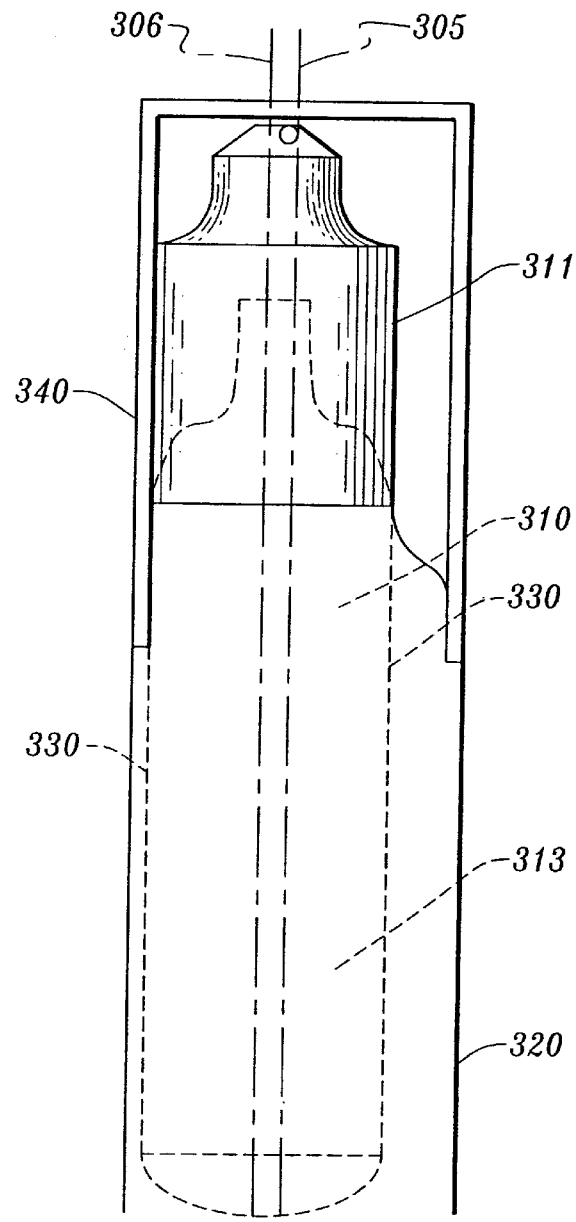
FIG. 3c schematically shows a side view of the third embodiment of the invention.

FIGS. 3a–b shows a third embodiment of the invention. In this embodiment, the holder 320 is cylindrical, but is fixedly, and not necessarily removably, attached to the dispenser 310, which can include a gas cartridge 313 and a dispenser head apparatus 311. Unlike the holder in previously described embodiments, the dispenser 310 need not, or alternatively cannot, be removed from the well 330 in the holder 320 during use. As with the previous embodiments, however, the well 330 and the holder 320 each define a separate axis to allow for the correct positioning of the centers of mass of the holder 320 and the dispenser 310 when held in the well 330 as further described in connection with FIGS. 4a–b.

Additionally, the holder 320 can be made from a plastic that glows in the dark to facilitate use of the dispenser at night. A cover 340 can be fixedly but detachably attached over the holder 320, using techniques known in the art, to enclose and protect the dispenser 310 when not in use. The cover 340 is preferably of clear plastic and may be used to facilitate marketing in the manner described in connection with the first embodiment of the invention.

With reference to FIGS. 1–4, in all of the embodiments described above, the holder 120, 220, 320 may be used to indicate the amount of product remaining in the dispenser 110, 210, 310 as follows. The holder with the seated dispenser 110, 210, 310 is laid on its side, so that the curvilinear circumference 125, 225, 325 rests on a flat, smooth, horizontal surface such as a table top 185, 285 as shown in FIGS. 1 and 2, with the axis of rotation 105, 205, 305 of the holder 120, 220, 320 (a central axis in the embodiments shown) approximately parallel to the surface. It will be noted that in the embodiment shown in FIG. 1, the central axis is tilted slightly from the horizontal. The shape of the holder 120, 220, 320, and the location of the well 130, 230, 330 in it, must cause the center of mass of the holder 120, 220, 320, and the center of mass of the fully seated dispenser 110, 210, 310 and the product it contains, to be positioned relative to the axis 105, 205, 305 of the holder such that as the weight of the product remaining in the dispenser 110, 210, 310 decreases as the dispenser is emptied, the holder 120, 220, 320 rolls about the axis 105, 205, 305 to unique points along the curvilinear circumference 125, 225, 325, thus providing an indicator of the amount of product remaining in the dispenser 110, 210, 310. Generally, this means that the axis of the well 106, 206, 306 in the holder (which in these embodiments is identical to the dispenser axis when the dispenser is seated in the well) must be displaced from the holder axis 105, 205, 305 by a prescribed degree. Additionally, in the first embodiment, the thickness of the base 121 can be varied to cause the center of mass of the holder 120 to be properly positioned relative to that of the dispenser 110. The relative amount of product remaining, corresponding to the degree of roll, may be indicated by appropriate indicator marks 180, 280, 380 on the bottom of the holder at the point where its edge contacts the table 185, 285, 385 or otherwise on the external surface of the holder, 120, 220, 320.

The holder may also include an indicator mark for a calibration position. When the empty holder 120, 220, 320 is laid on a sufficiently flat, smooth and horizontal surface, it will assume a specific angular position, so that the curvilinear circumference 225, 325 rests with a particular point touching the table 285, 385 as indicated by a dot 255, 355 in FIGS. 2b and 3b. If this position is not assumed, the surface is not sufficiently flat, smooth or horizontal at that location, and the holder must be moved to a location where it assumes the calibration position. When the dispenser is placed in the holder at that location, the holder will then assume an angular position that accurately indicates the amount of agent remaining in the dispenser.

The change of weight due to use of the product may be relatively small: for example, the 60-gram weight of the completely full $CO_2$ cartridge described above, which contains 16 grams of $CO_2$, changes by only 27% as it is emptied. Therefore, it is important that the holder 120, 220, 320 be designed so that there is a sufficient degree of angular roll over the range of possible combined weights of the dispenser and product—for example, enough to allow the user to easily read the changes shown by the indicator marks 180, 280, 380.

FIG. 4 illustrates the dependence of the degree of roll on the relative locations of the center of mass of the holder and the well with the dispenser in place, and on the relative masses of the holder and dispenser. The analysis shown is only approximate for the first embodiment in that it does not take into account the slight tilt of axis of the holder and dispenser from horizontal when they are laid on a table without the cover as shown in FIG. 1c. The analysis is accurate, however, for the case of the second and third embodiment, and is also accurate for the case in which the first embodiment is used with the cover in place.

As shown in FIG. 4a the dispenser/product and holder's effective masses $M_v$ and M are located at radial distances $R_1$ and $R_2$ from the center of rotation (in this case the central axis) of the holder, each respectively subtending variable angles $\theta_v$ and $\theta_2$ from the horizontal for $M_v R_1 / M R_2 = 1$ and with fixed supplementary angle $\theta$ between them shown in the equation in FIG. 4c. The gravitational forces on masses $M_v$ and M are resolved into tangential forces $F_1$ and $F_2$ acting at moment distances $R_1$ and $R_2$ as in the equations of FIGS. 4d and 4e. Free rotation of the holder occurs until the moments $F_1 R_1$ and $F_2 R_2$ are equal per the equation shown in FIG. 4f as in FIG. 4b. These relations combine to give the equation shown in FIG. 4g which implicitly relates the variable angle $\theta_v$ to the parameter $M_v R_1 / M R_2$ and the fixed angle $\theta$, as shown graphically in FIG. 5a.

Alternatively, a more convenient variable angle of rotation $\theta_r$ may be defined as in the equation shown in FIG. 4h, which is the angular change from the initial position of the holder with the full dispenser in place. The horizontal position of $\theta_r = 0$ can be selected for the initial full condition of the dispenser, where $M_v R_1 / M R_2 = 1$, although this selection is arbitrary and other initial positions can be chosen without changing the basic principles of operation. For example, an increase in sensitivity may be obtained by selecting a initial position other than horizontal, although aesthetically such a construction may be less pleasing to the user. The relations in the equations of FIGS. 4g and 4h may then be combined to compute the plots shown in FIG. 5b. The change in $\theta_r$ as the dispenser is emptied is shown graphically in FIG. 5b for various fixed angles $\theta$. Therefore, for given design values of M, $R_1$, $R_2$ and $\theta$, there is a direct relationship between the mass of the dispenser and product $M_v$ and the angles $\theta_v$ or $\theta_r$ at which the rolling holder comes to rest.

Figure 5A:
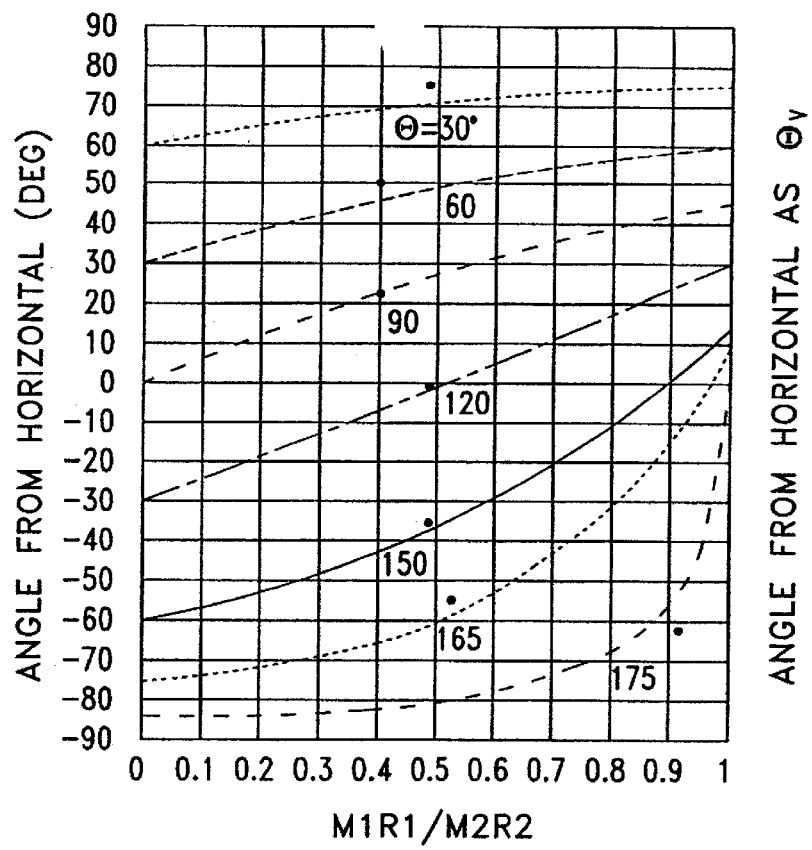
FIG. 5a graphically shows the angular roll of the dispenser/product and the holder as a function of the mass and position of the dispenser/product in the holder where the angular position of the mass from horizonal is defined as $\theta_y$.
Figure 5B:
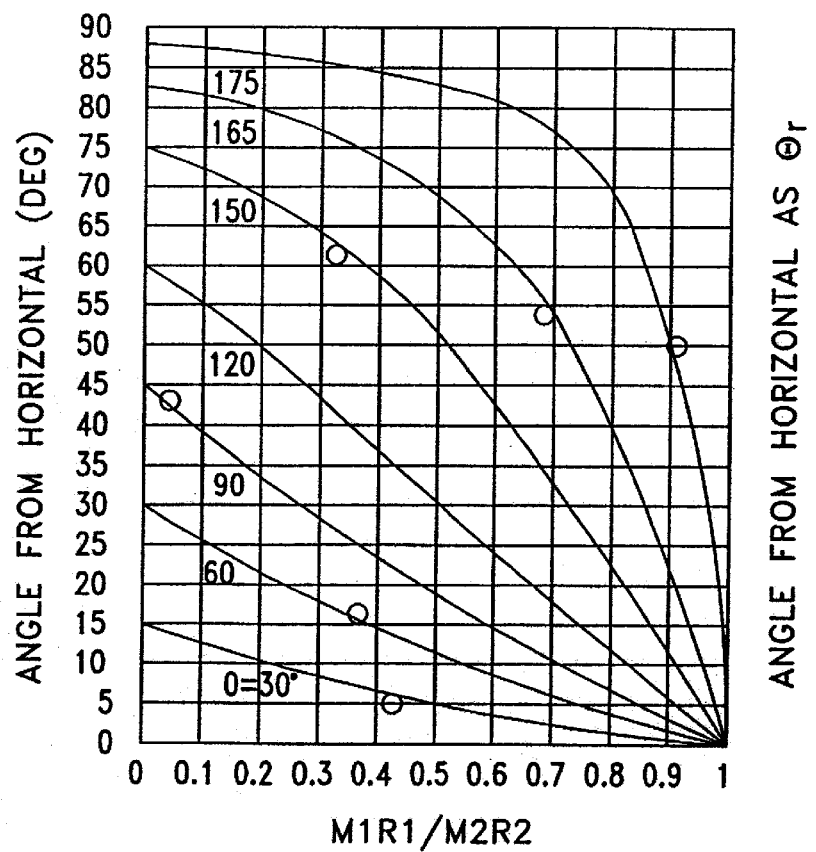
FIG. 5b graphically shows the angular roll of the dispenser/product and the holder as a function of the mass and position of the dispenser/product in the holder where the angle of displacement of the holder from its initial horizonal position is defined as $\theta_r$.

It can be seen from the plots of $\theta_v$ and $\theta_r$ in FIGS. 5a and 5b that a reduction in dispenser/product mass $M_v$ of 27% as it empties, corresponding to a change in parameter $M_v R_1 / M R_2$ from 1.00 to 0.73, results in a very small (e.g.,<10°) change in the angle of rest (when the holder is at equilibrium) of $\theta_v$ and $\theta_r$ for small values of fixed angle $\theta$ (e.g. <90°). At very large values of $\theta$ (approaching 180°), the change in rest angles $\theta_v$ and $\theta_r$ approaches 90°, but the position of rest becomes relatively unstable due to insufficient rolling torque and the holder can roll continuously under perturbations such as a slight table tilt or breeze, or can refuse to roll to the stable position due to a slight table roughness. An optimum choice lies between these extremes.

The choice depends on the fractional change in of $M_v$ as the dispenser is emptied of product and the desired responsive change in the variable angle, whether expressed as $\theta_v$ or $\theta_r$. It is usually desirable to have the responsive change in $\theta_v$ and $\theta_r$ be approximately linear over the possible range of $M_v$; however, this is not a requirement for use, as the indicator marks 180, 280, 380 may be adjusted to allow for a non-linear response. The approximate point at which response becomes significantly non-linear for various fixed angles $\theta$ is indicated in FIG. 5b by a "0" on each plot, where the slope has changed by a factor of 2 from the initial slope at $M_v R_1/MR_2=1$. Although linearity of response is not required, it is important that the indicator marks be adequately spaced to allow the user to easily read the indicator marks, and the change in $\theta_v$ and $\theta_r$ must be large enough to allow for such spacing.

By way of example, if a linear response is desired, it can be seen in FIGS. 5a and 5b that the percentage change in $M_v$ must be approximately 9%, 27%, 48% and 80% for $\theta$ equal to 175°, 165°, 150°, and 120°, respectively. For the 27% change of $M_v$ associated with the $CO_2$ cartridge described above, the optimum choice of fixed angle $\theta$ is about 165° as this results in a responsive change of the variable angles $\theta_v$ and $\theta_r$ to changes in $M_v$ of about 50° which is sufficient to allow for adequate spacing of the indicator marks. A choice of 150° for angle e would give greater linearity and stability, but at the cost of a reduced response in the variable angle to 30°. A choice of 175° for $\theta$ would give an initially higher roll sensitivity when the cartridge is nearly fill, and a larger change of 75° for $\theta_v$ and $\theta_r$, but at the critical juncture where the cartridge is nearly empty, this choice results in a low and highly non-linear response in $\theta_v$ and $\theta_r$. While acceptable design choices for $\theta$ fall within the range of greater than 150° and less than 175°, the choice of $\theta$ near 165° provides a high roll sensitivity together with good roll linearity and stability.

While preferred embodiments of the present invention are described above and in the following claims, it is contemplated that various modifications may be made without departing from the spirit and scope of the invention. For example, any generally cylindrical form with a partially curvilinear circumference, for example, based on an oval, for which a one-to-one relationship between the center of mass and position when resting on its side on a substantially flat, horizontal surface, can be determined, could replace the substantially circular cylindrical form shown in the embodiments.

What is claimed is:

1. A container comprising:

a holder having an effective mass of value M and defining an axis of rotation and an at least partially curvilinear external circumference; said holder further defining a well adapted to receive, and retain in a selected position, a selected dispenser for containing and dispensing a consumable product, wherein the dispenser and consumable product contained in the dispenser together have an effective mass having a value $M_v$ when retained in the selected position, and wherein the mass $M_v$ varies in response to the amount of consumable product contained in the dispenser; said holder adapted to rotate about the axis of rotation along the curvilinear circumference when the curvilinear external circumference is placed on a substantially horizontal and smooth surface and the axis of rotation is substantially parallel to such surface; and wherein the well is positioned in the holder such that when the dispenser and consumable product contained in the dispenser are retained in the well in the selected position, and the curvilinear circumference is placed on the substantially horizontal and smooth surface with the axis of rotation substantially parallel to such surface, the effective mass of the dispenser is a first radial distance $R_1$ from the axis of rotation, the effective mass of the holder is a second radial distance $R_2$ from the axis of rotation, and the effective mass of the holder is positioned at a fixed angle of value $\theta$ relative to the effective mass of the dispenser, measured about the axis of rotation, wherein $\theta$ is between 90° and 175°, such that, when the holder is at a position of equilibrium, the effective mass of the dispenser is positioned at a variable angle about the axis of rotation, having a value $\theta_v$, according to the equation: $\theta_v = 180° - \theta - a\cos(\alpha \cos \theta_v)$ where $\alpha = R_1 M_v / R_2 M$, whereby the value $\theta_v$ measured from the horizontal is uniquely associated with a specific amount of consumable product contained in the dispenser; and wherein the holder comprises an indicator mark for indicating a selected value of the angle $\theta_v$ associated with a particular amount of consumable product contained in the dispenser, whereby a user may determine the approximate amount of consumable product contained in the dispenser.

2. The container according to claim 1 fisher comprising a cover removably attachable to the holder, such the cover and holder are adapted to fully enclose the dispenser when said dispenser is fixedly retained in the well.

3. The container according to claim 2 wherein the cover is composed of clear plastic.

4. The container according to claim 2 wherein the dispenser comprises a top portion defining a sealable aperture for controllably dispensing the consumable product, and a bottom portion opposite the top portion, and the well is adapted to receive and fixedly retain part of the bottom portion and part the top portion of the dispenser.

5. The container according to claim 4 wherein the dispenser defines an external circumference, and the cover further comprises an inside surface and a restraining device comprising an interior retainer component, said restraining device comprising a retainer component forming a cut out portion, said restraining device fixedly attached to the inside surface of the cover, such that when the cover is attached to the holder, the cut out portion is adapted to fit along the external circumference of the dispenser when the dispenser is fixedly held in the well, thereby impeding movement of the dispenser.

6. The container according to claim 1 wherein the well is adapted to fixedly but releaseably retain the dispenser in the selected position.

7. The container according to claim 1 wherein the well and holder are adapted to fixedly hold the dispenser in a substantially upright position when the axis of rotation is substantially vertical.

8. The container according to claim 1 wherein the indicator mark is associated with a first preselected value of mass $M_v$, such that when mass $M_v$ has approximated the first preselected value, and the curvilinear external circumference is placed on the substantially horizontal and smooth surface with the axis of rotation substantially parallel to such surface, the indicator mark is positioned at a preselected location relative to the surface and further comprising an additional indicator mark associated with a second preselected value of mass $M_v$, such that when mass $M_v$ has approximated the second preselected value, and the curvilinear external circumference is placed on the substantially horizontal and smooth surface with the axis of rotation substantially parallel to such surface, the additional indicator mark is positioned at the preselected location.

9. The container according to claim 8, wherein the indicator mark is positioned adjacent to the surface when the mass $M_v$ is approximately equal to the first preselected value and the additional indicator mark is positioned adjacent to the surface when the mass $M_v$ is approximately equal to the second preselected value.

10. The container according to claim 1 wherein the well is adapted to fixedly hold the dispenser when the consumable product is dispensed.

11. The container according to claim 1 wherein the dispenser comprises a cartridge adapted to contain a pressurized gas.

12. The container according to claim 1 wherein the holder is a substantially circular cylinder.

13. The container according to claim 12 wherein the dispenser comprises a top portion defining a sealable aperture for controllably dispensing the consumable product, and a bottom portion opposite the top portion, and the well is adapted to receive and fixedly and releaseably retain part of the bottom portion and part the top portion of the dispenser.

14. The container according to claim 1 wherein the holder is a substantially semicircular cylinder.

15. The container according to claim 1 wherein $\alpha$ varies between a maximum value of approximately 1.00 and a minimum value of approximately 0.73 and wherein $\theta$ is between 150° and 175°.

16. The container according to claim 1 wherein a varies between a maximum value of approximately 1.00 and a minimum value of approximately 0.73 and wherein $\theta$ is approximately 165°.

17. The container according to claim 1 wherein the holder is formed of florescent plastic.

18. The container according to claim 1 wherein the dispenser comprises a top portion defining a sealable aperture for controllably dispensing the consumable product, and a bottom portion opposite the top portion, and the well is adapted to receive and fixedly and releaseably retain the bottom portion of the dispenser.

19. The container according to claim 1 wherein the dispenser comprises a top portion defining a sealable aperture for controllably dispensing the consumable product, and a bottom portion opposite the top portion, and the well is adapted to receive and fixedly retain the bottom portion of the dispenser.

20. In a container comprising a holder having an effective mass of value M and defining an axis of rotation and an at least partially curvilinear external circumference; said holder further defining a well adapted to receive, and retain in a selected position, a selected dispenser for containing and dispensing a consumable product, wherein the dispenser and consumable product contained in the dispenser together have an effective mass having a value $M_v$ when retained in the selected position, and where the mass $M_v$ varies in response to the amount of consumable product contained in the dispenser; said holder adapted to rotate about the axis of rotatation along the curvilinear circumference when the curvilinear external circumference is placed on a substantially horizontal and smooth surface and the axis of rotation is substantially parallel to such surface; and wherein the well is positioned in the holder such that when the dispenser and consumable product contained in the dispenser are retained in the well in the selected position, and the curvilinear circumference is placed on the substantially horizontal and smooth surface with the axis of rotation substantially parallel to such surface, the effective mass of the dispenser is a first radial distance $R_1$ from the axis of rotation, the effective mass of the holder is a second radial distance $R_2$ from the axis of rotation, and the effective mass of the holder is positioned at a fixed angle of value $\theta$ relative to the effective mass of the dispenser, measured about the axis of rotation, such that, when the holder is at a position of equilibrium, the effective mass of the dispenser is positioned at a variable angle about the axis of rotation, having a value $\theta_v$, whereby the value $\theta_v$ measured from the horizontal is uniquely associated with a specific amount of consumable product contained in the dispenser; and wherein the holder comprises an indicator mark for indicating a selected value of the angle $\theta_v$ associated with a particular amount of consumable product contained in the dispenser, the method of selecting fixed angle comprising the steps of:

defining a first value of $\alpha$ when the dispenser is full, where $\alpha = R_1 M_v / R_2 M$;

calculating a second value of $\alpha$ associated with the value of $M_v$ when the dispenser is empty;

choosing $\theta$ such that $\theta$ is between 90° and 175° and such that a first value of $\theta_v$ when the dispenser is full minus a second value of $\theta_v$ when the dispenser is empty, where $\theta_v$ is $180°-\theta-\mathrm{acos}(\alpha \cos \theta_v)$, is maximized while retaining sufficient sensitivity of response for all values of $\theta_v$ between the first value and the second value.

21. The method according to claim 20 wherein the choosing step further comprises:

choosing $\theta$ so that, as the dispenser is emptied, the first value of $\theta_v$ changes to the second value of $\theta_v$ in a substantially linear fashion.

22. The method according to claim 20 wherein the choosing step further comprises choosing $\theta$ such that the first value minus the second value is greater than 50 degrees.

23. A container comprising:

a holder having an effective mass of value M and defining an axis of rotation and an at least partially curvilinear external circumference; said holder further defining a well adapted to receive, and retain in a selected position, a selected dispenser for containing and dispensing a consumable product, wherein the dispenser and consumable product contained in the dispenser together have an effective mass having a value $M_v$ when retained in the selected position, and wherein the mass $M_v$ varies in response to the amount of consumable product contained in the dispenser; said holder adapted to rotate about the axis of rotation along the curvilinear circumference when the curvilinear external circumference is placed on a substantially horizontal and smooth surface and the axis of rotation is substantially parallel to such surface; and wherein the well is positioned in the holder such that when the dispenser and consumable product contained in the dispenser are retained in the well in the selected position, and the curvilinear circumference is placed on the substantially horizontal and smooth surface with the axis of rotation substantially parallel to such surface, the effective mass of the dispenser is a first radial distance $R_1$ from the axis of rotation, the effective mass of the holder is a second radial distance $R_2$ from the axis of rotation, and the effective mass of the holder is positioned at a fixed angle of value $\theta$ relative to the effective mass of the dispenser, measured about the axis of rotation, wherein $\theta$ is between 90° and 175°, such that, when the holder is at a position of equilibrium, the effective mass of the dispenser is positioned at a variable angle about the axis of rotation, having a value $\theta_v$, according to the equation: $\theta_v = 180° - \theta - \mathrm{acos}(\alpha \cos \theta_v)$ where $\alpha = R_1 M_v / R_2 M$, whereby the value $\theta_v$ measured from the horizontal is uniquely associated with a specific amount of consumable product contained in the dispenser; and wherein the holder comprises at least two indicator marks for indicating a selected value of the angle $\theta_v$ associated with a particular amount of consumable product contained in the dispenser and a unique preselected value of the mass $M_v$, such that when the mass $M_v$ has approximated the unique preselected value, and the curvilinear external circumference is placed on the substantially horizontal and smooth surface with the axis of rotation substantially parallel to such surface, the indicator mark associated with the selected value of angle $\theta_v$ positioned adjacent to the surface, whereby a user may determine the approximate amount of consumable product remaining in the dispenser said container further comprising a cover removably attachable to the holder, such the cover and holder are adapted to fully enclose the dispenser when said dispenser is fixedly retained in the well.

* * * * *